(12) United States Patent
Kidooka

(10) Patent No.: US 6,969,389 B2
(45) Date of Patent: Nov. 29, 2005

(54) BIPOLAR HEMOSTATIC FORCEPS FOR AN ENDOSCOPE

(75) Inventor: Satoshi Kidooka, Tokyo (JP)

(73) Assignee: PENTAX Corporation, Tokyo (JP)

( * ) Notice: Subject to any disclaimer, the term of this patent is extended or adjusted under 35 U.S.C. 154(b) by 112 days.

(21) Appl. No.: 10/404,556

(22) Filed: Apr. 2, 2003

(65) Prior Publication Data

US 2005/0075631 A1  Apr. 7, 2005

(30) Foreign Application Priority Data

Apr. 9, 2002  (JP)  ............................. 2002-106010

(51) Int. Cl.$^7$ ............................................ A61B 18/12
(52) U.S. Cl. ......................................... 606/51; 606/49
(58) Field of Search ............................ 606/49–52, 205

(56) References Cited

U.S. PATENT DOCUMENTS

| | | | |
|---|---|---|---|
| 6,451,018 B1 * | 9/2002 | Lands et al. ................... | 606/50 |
| 6,767,349 B2 * | 7/2004 | Ouchi ........................... | 606/51 |
| 2002/0123667 A1 | 9/2002 | Ouchi | |

FOREIGN PATENT DOCUMENTS

| | | |
|---|---|---|
| JP | 10-151143 | 6/1998 |
| JP | 10-155798 | 6/1998 |
| JP | 11-019086 | 1/1999 |
| JP | 11-019087 | 1/1999 |
| JP | 11-155878 | 6/1999 |
| JP | 2000-271128 | 10/2000 |
| JP | 2002-253570 | 9/2002 |

* cited by examiner

*Primary Examiner*—Roy D. Gibson
*Assistant Examiner*—Aaron Roane
(74) *Attorney, Agent, or Firm*—Greenblum & Bernstein, P.L.C.

(57) ABSTRACT

The bipolar hemostatic forceps for an endoscope includes an inserting portion to be inserted into a body cavity through the endoscope, first and second electrodes mounted to a distal end of the inserting portion, and an insulator located between the first and second electrodes to insulate the first and second electrodes from each other except at the front portions thereof. The first and second electrodes are movable between an open position and a closed position so as to be able to pinch a bleeding portion between the front portions thereof. The first and second electrodes are supplied with high frequency electric power to generate high frequency current flowing through the bleeding portion pinched therebetween and thereby stop bleeding of that portion. The insulator is formed in a shape that restricts the swinging angles of the first and second electrodes.

9 Claims, 8 Drawing Sheets

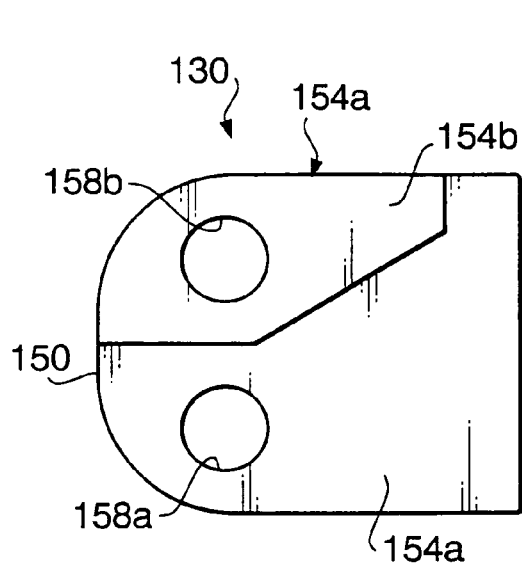
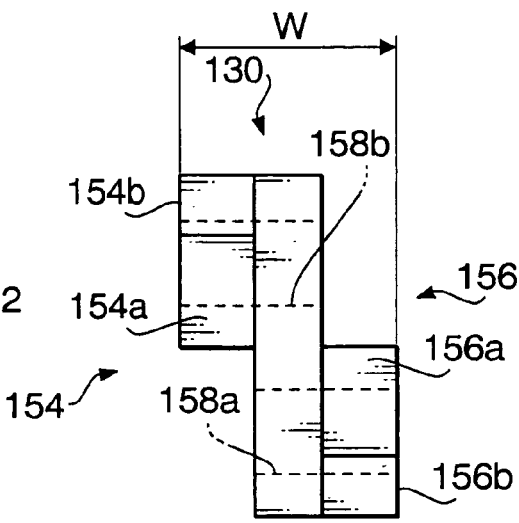
FIG.6A  FIG.6B
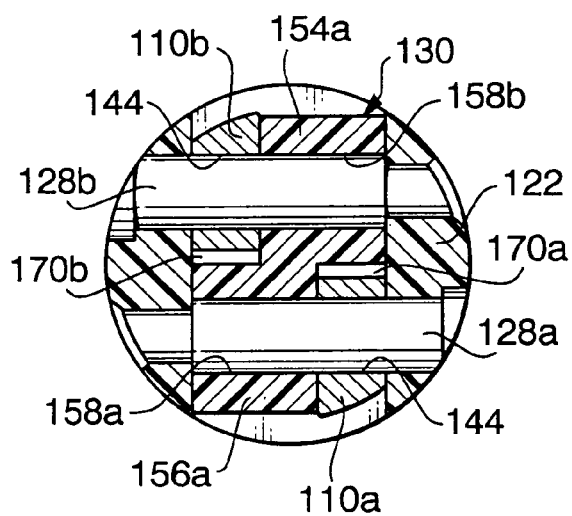
FIG. 7

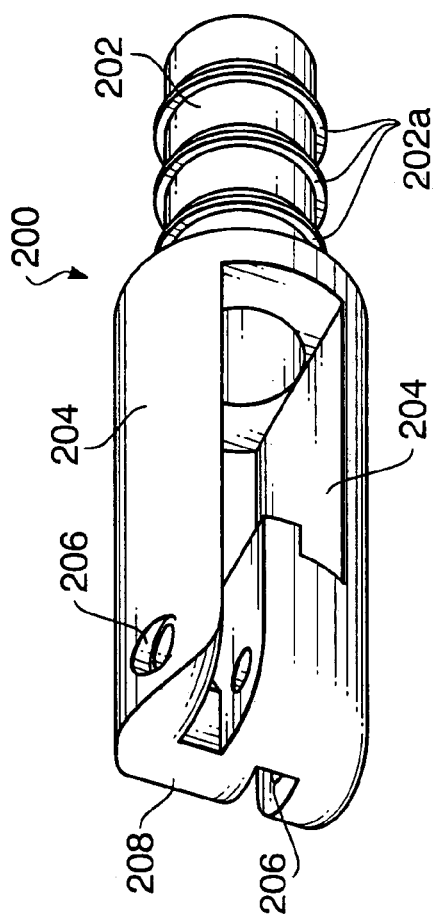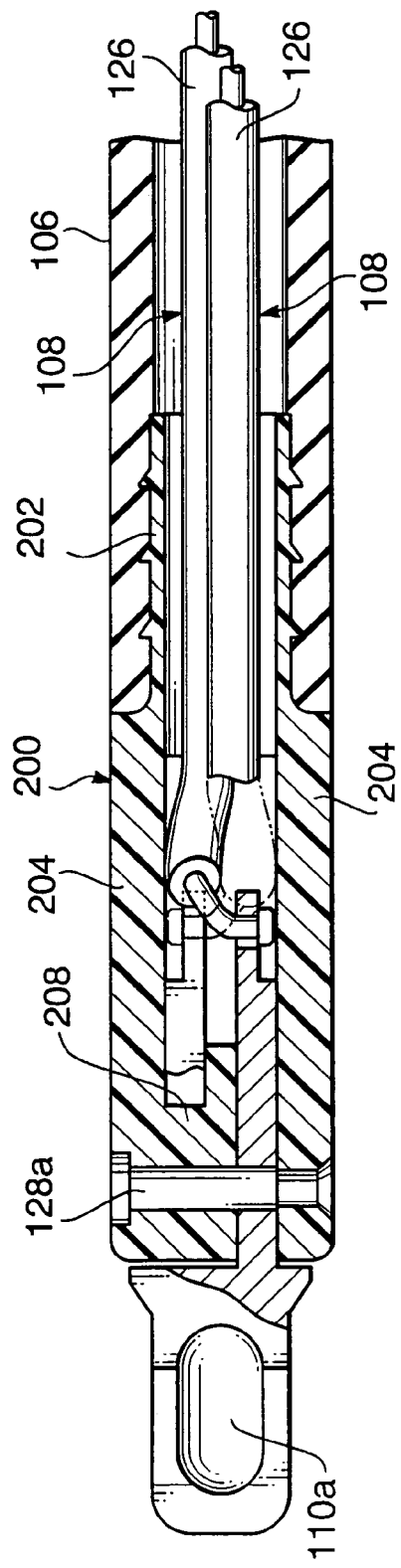
FIG. 8
FIG. 9

BIPOLAR HEMOSTATIC FORCEPS FOR AN ENDOSCOPE

BACKGROUND OF THE INVENTION

The present invention relates to a bipolar hemostatic forceps having a pair of electrodes at a distal end of an inserting portion to be inserted into a body cavity through an endoscope.

A monopolar high frequency treatment tool is commonly used for endoscopic surgery. The monopolar high frequency treatment tool utilizes an electrode in combination with a counter plate attached to the body surface of a patient so that high frequency current flows between the electrode and the counter plate.

In the surgery utilizing the monopolar high frequency treatment tool, electric leak may occur if the patient comes in contact with a conductor other than the counter plate, which causes decrease of current effective to the operation and/or the surgeon to get burned.

Japanese patent provisional publication No. P2000-271128 discloses a bipolar high frequency treatment tool that overcomes the disadvantages of the monopolar high frequency treatment tool. The treatment tool disclosed in the above mentioned publication has a pair of electrodes mounted at the distal end of the treatment tool. The electrodes are arranged so as to open and close like pincers by a remote manipulation from the proximal end of the treatment tool. The electrodes are connected to the positive and negative terminals of a high frequency power supply, respectively, so that high frequency current flows through the tissue of the patient pinched between the electrodes.

The treatment tool disclosed in the above-mentioned publication is designed as a biopsy forceps and the pair of electrodes provided thereto opens widely to effectively sample tissue. Therefore, if this treatment tool is utilized as a hemostatic forceps for stopping bleeding of a blood vessel, the pair of electrodes pinch not only the blood vessel but also a large portion of tissue around the blood vessel. As a result, the hemostasis of the blood vessel cannot be carried out efficiently and not only the blood vessel but also the tissue therearound get heated.

Thus, there is a need for a bipolar hemostatic forceps that is capable of pinching a bleeding portion between a pair of electrodes thereof without pinching also a large portion of tissue around the bleeding portion.

SUMMARY OF THE INVENTION

The invention is advantageous in that a bipolar hemostatic forceps and an electrode assembly that satisfy the above-mentioned need are provided.

According to an aspect of the invention, there is provided a bipolar hemostatic forceps for an endoscope which includes an inserting portion to be inserted into a body cavity through the endoscope, first and second electrodes mounted to a distal end of the inserting portion, and an insulator located between the first and second electrodes to insulate the first and second electrodes from each other except at the front portions thereof. The first and second electrodes are movable between an open position and a closed position so as to be able to pinch a bleeding portion between the front portions thereof. The first and second electrodes are supplied with high frequency electric power to generate high frequency current flowing through the bleeding portion pinched therebetween and thereby stop bleeding of that portion. The insulator is formed in a shape that restricts the swinging angles of the first and second electrodes so that the first and second electrodes do not pinch a large portion around the bleeding portion which may decrease the efficiency of hemostasis.

In another aspect of the invention, an electrode assembly is provided, which is to be mounted to a distal end of an inserting portion of a bipolar hemostatic forceps that is to be inserted into a body cavity through an endoscope. The electrode assembly includes a supporting member that is to be mounted to the distal end of the inserting portion of the bipolar hemostatic forceps, first and second electrodes held by the supporting member, and an insulator located between said first and second electrodes. The first and second electrodes are swingable to open and close the front portions thereof. Further, the first and second electrodes are adapted to be supplied with high frequency electric power to generate high frequency current between the front portions. The insulator insulates the first and second electrodes from each other except at the front portions thereof. The insulator is formed in a shape that restricts the swinging angles of the first and second electrodes.

In an embodiment of the invention, the insulator of the above-mentioned bipolar high frequency hemostatic forceps and/or electrode assembly has first and second side surfaces which face the first and second electrodes, respectively. The first and second side surfaces are provided with first and second protrusions, respectively, that abut against the first and second electrodes to restrict the swinging angles of the first and second electrodes.

Optionally, the supporting member has two arms extending in parallel to each other to form a slit therebetween. The insulator is integrally formed to the supporting member within the slit with the first and second protrusions connected to the arms of supporting member.

Optionally, the bipolar hemostatic forceps and/or the electrode assembly include first and second pins that penetrate the insulator through the first and second side surfaces. The first pin pivotably supports the first electrode in the vicinity of the first side surface and the second pin pivotably supports the second electrode in the vicinity of the second side surface, so that allow the first and second electrodes to open and close.

In the above case, the first protrusion of the insulator is formed such that it surrounds the second pin in the vicinity of the first electrode and the second protrusion of the insulator is formed such that it surrounds the first pin in the vicinity of the second electrode in order to prevent the first and second electrodes from coming into contact with the second and first pins, respectively.

Further optionally, the insulator is provided with two through holes having slightly smaller inner diameters than the outer diameters of the first and second pins, and the first and second pins penetrate the insulator by being inserted through respective one of the two through holes.

BRIEF DESCRIPTION OF THE ACCOMPANYING DRAWINGS

FIG. 1 schematically shows a bipolar hemostatic forceps according to an embodiment of the invention connected to a high frequency power supply;

Figure 1:
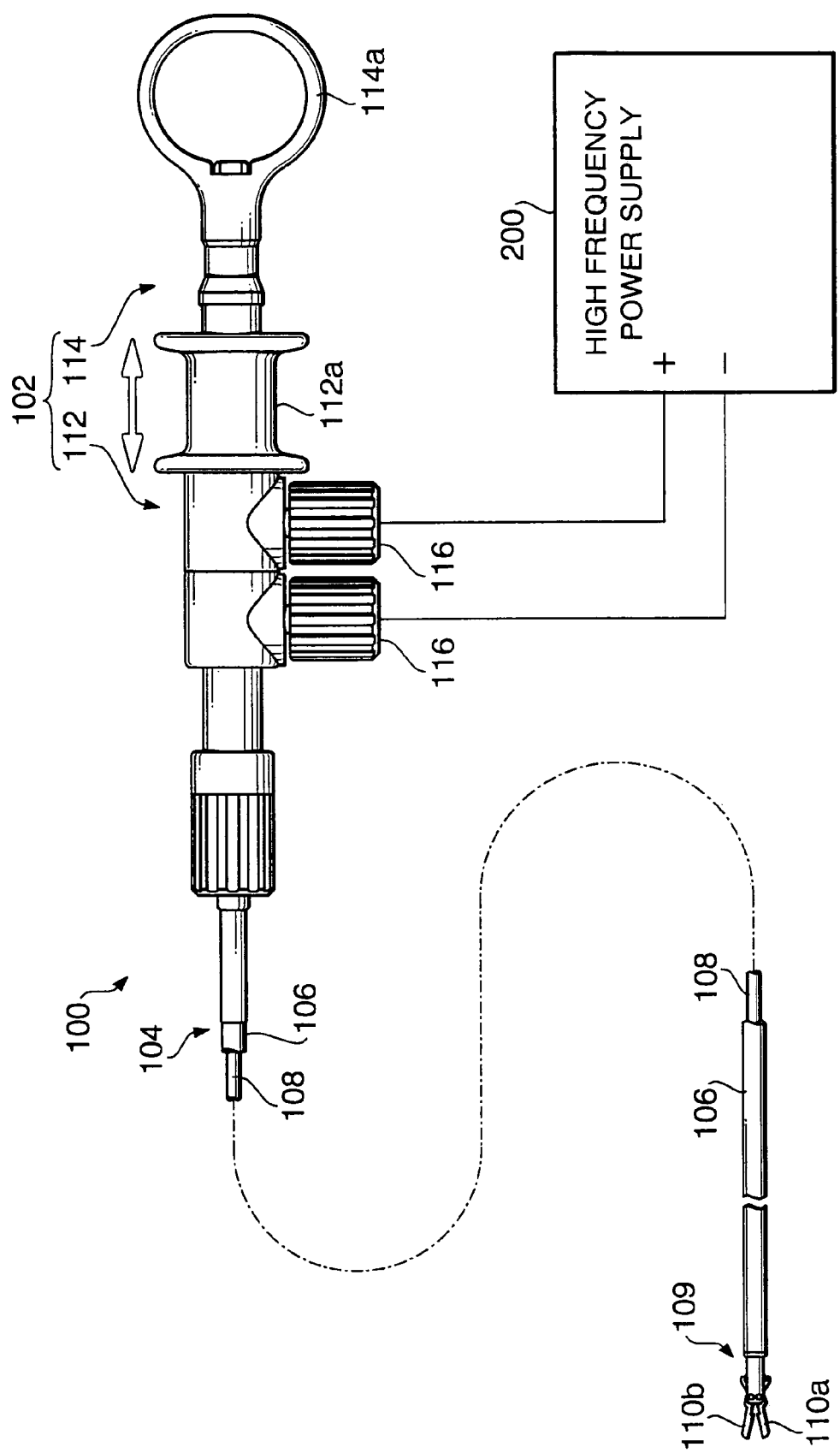
Figure 3A:
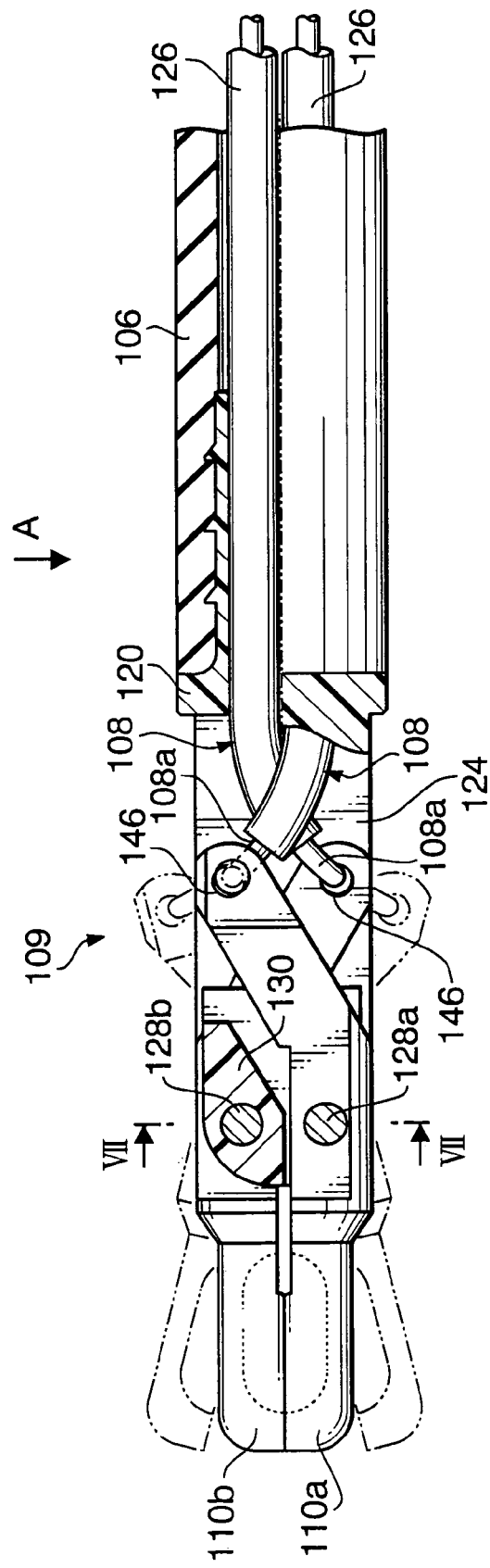
FIGS. 3A and 3B are partially sectional side views of the distal end of the bipolar hemostatic forceps shown in FIG. 1.

FIGS. 6A and 6B respectively show a right side view and a rear side view of an insulating block of the bipolar hemostatic forceps shown in FIG. 1;

FIG. 7 is a sectional view of the electrode assembly taken along the line VII—VII in FIG. 3A FIG. 8 is a perspective view of a variation of a supporting member of the bipolar hemostatic forceps shown in FIG. 1; and FIG. 9 is a sectional view of the an end portion of an bipolar hemostatic forceps according to an embodiment of the invention in which the supporting member shown in FIG. 8 is utilized.

DETAILED DESCRIPTION OF THE EMBODIMENTS

Hereinafter, an embodiment of the invention will be described with reference to the accompanying drawings.

FIG. 1 schematically shows a bipolar hemostatic forceps 100 according to an embodiment of the invention connected to a high frequency power supply 200.

The hemostatic forceps 100 includes an operation portion 102 and an inserting portion 104 connected to the distal end of the operation portion 102.

The inserting portion 104 is provided in a form and size that allows it to be introduced into a body cavity through a treatment tool inserting channel of an endoscope (not shown). The inserting portion 104 includes an elongated, flexible sheath 106, and a pair of conductive wires 108 (only one is shown) slidably passed through the sheath 106. The sheath 106 is made of insulating material such as poly-tetra-fluoro-ethylene (PTFE). In an exemplary embodiment, the sheath 106 is 1 m to 2 m long and has an outer diameter of 2 mm to 3 mm.

An electrode assembly 109 is mounted to the distal end of the insertion portion 104. The electrode assembly 109 includes first and second electrodes 110a and 110b that are connected to the conductive wires 108.

The operation portion 102 includes a cylindrical portion 112 and a rod portion 114 slidably inserted into the cylindrical portion 112.

The cylindrical portion 112 has a circumferential groove 112a at a proximal end thereof. A user of the hemostatic forceps 100 can hold the operation portion 112 by pinching it at the groove 112a with his index finger and long finger.

The rod portion 114 has a ring 114a into which the user can insert his thumb to slide the rod portion 114 within the cylindrical portion 112 back and forth.

The rod portion 114 is connected with the pair of wires 108 in the cylindrical portion 112 such that the wires 108 retract and proceed in the sheath 106 as the rod portion 114 is moved back and forth with respect to the cylindrical portion 112. It should be noted that the pair of wires 108 may be fixed to each other so that they slide integrally within the sheath 106 to move the pair of electrodes 110 simultaneously.

The conductive wires 108 are detachably connected to power supply lines of the high frequency power supply 200 via a pair of connectors 116 provided to the side surface of the cylindrical portion 112. One of the conductive wires 106 is connected to the positive terminal of the power supply 200 and the other to the negative terminal.

Figure 2:
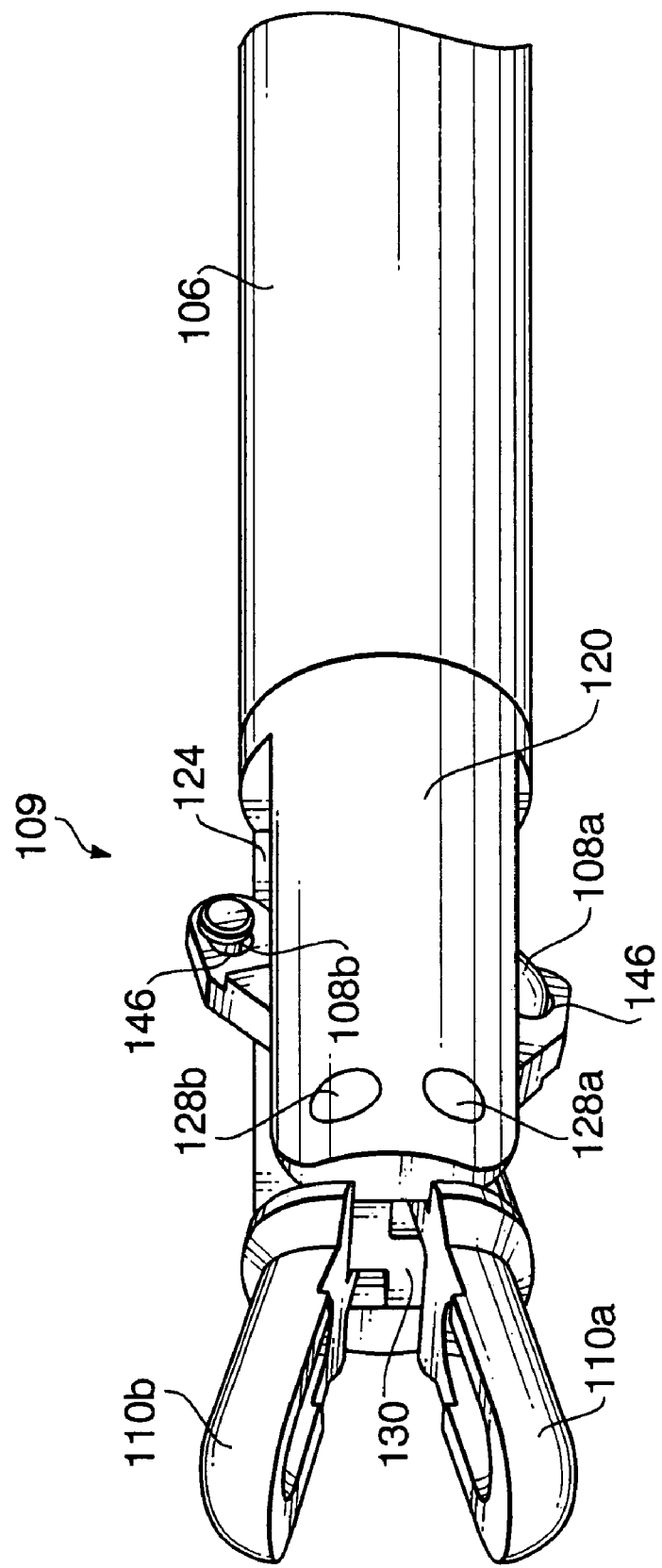
FIG. 2 is a perspective view of the distal end of the bipolar hemostatic forceps shown in FIG. 1.
Figure 3B:
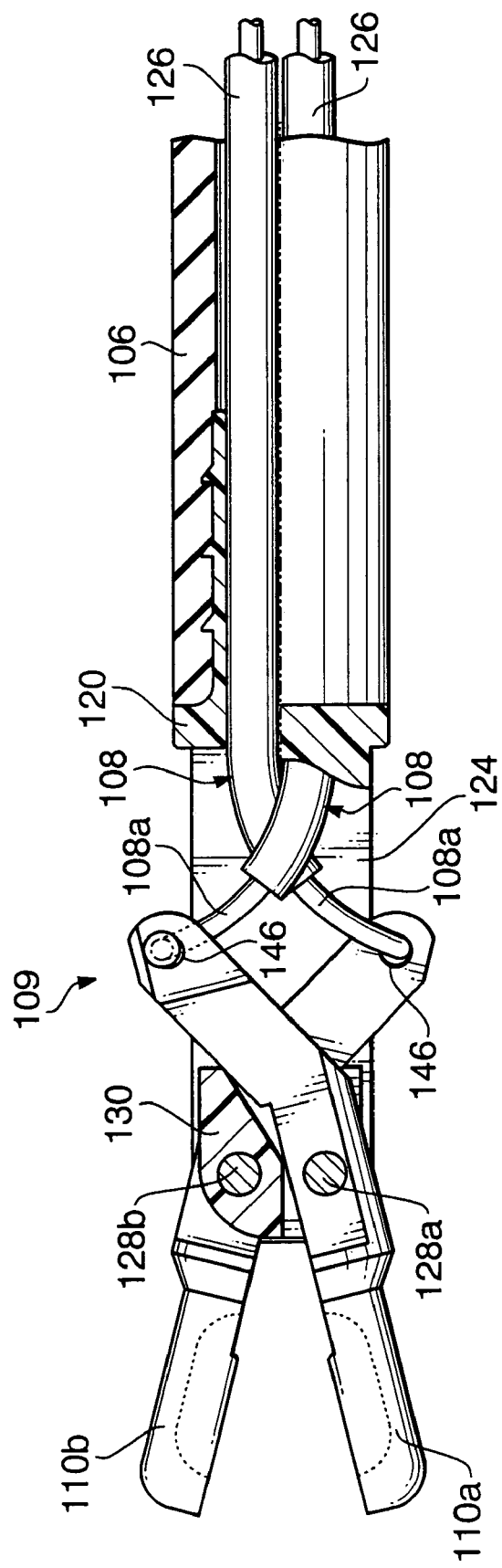
Figure 4:
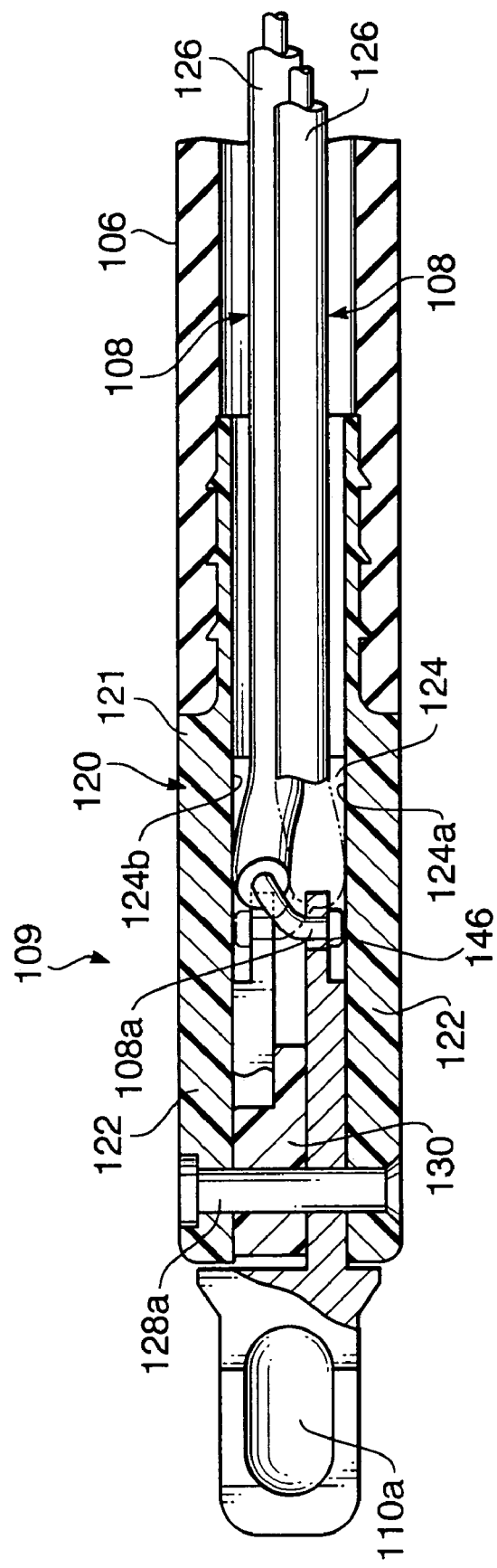
FIG. 4 is a sectional view of the bipolar hemostatic forceps shown in FIG. 3A observed from the direction indicated by an arrow A.

FIG. 2 is a perspective view of the distal end of the hemostatic forceps 100 shown in FIG. 1. FIGS. 3A and 3B are partially sectional side views of the distal end of the hemostatic forceps 100 shown in FIG. 1, and FIG. 4 is a sectional view of the distal end of the hemostatic forceps 100 shown in FIG. 3A observed from the direction indicated by the arrow A. Note that FIGS. 3A, 3B and 4 are drawn as a composite view combining cross sectional views at various positions.

The electrode assembly 109 includes a supporting member 120 for pivotably supporting the first and second electrodes 110a and 10b. The supporting member 120 is made of hard insulating material such as rigid plastic and mounted to the distal end of the flexible sheath 106.

As shown in FIG. 4, the supporting member 120 has a base 121 connected to the distal end of the flexible sheath 106 and two arms 122 extending forwards from the base 121 in parallel to each other to form a slit 124 therebetween having a constant width. First and second pins 128a and 128b are supported by the arms 122 in the vicinity of the distal end of the arms 122 (see also FIG. 3A).

The first and second pins 128a and 128b are held parallel to and spaced apart from each other, and perpendicular to first and second inner side surfaces 124a and 124b of the slit 124. The first and second pins 128a and 128b are made of stainless steel, for example.

The first and second electrodes 110a and 110b are partially inserted into the slit 124 of the supporting member 120 and pivotably mounted to the first and second pins 128a and 128b. Thus, the electrodes 110a and 110b can move between a closed position, at which the electrodes 110a and 110b come into contact with each other as shown in FIG. 3A, and an open position, at which the electrodes 110a and 110b are located apart from each other as shown in FIG. 3B.

As shown in FIGS. 3A and 3B, the rear ends or proximal ends of the electrodes 110a and 110b are connected with the respective conductive wires 108. Each of the conductive wires 108 is covered with a insulating tube 126 except the end portion 108a thereof at which the conductive wire 108 is connected to the corresponding electrode (110a, 110b).

An insulating block 130 is provided in the slit 124 of the supporting member 120 to prevent the first and second electrodes 110a and 110b from coming into contact to each other within the slit 124. The insulating block 130 is located between the first and second electrodes 110a and 110b and supported by the first and second pins 128a and 128b.

Figure 5:
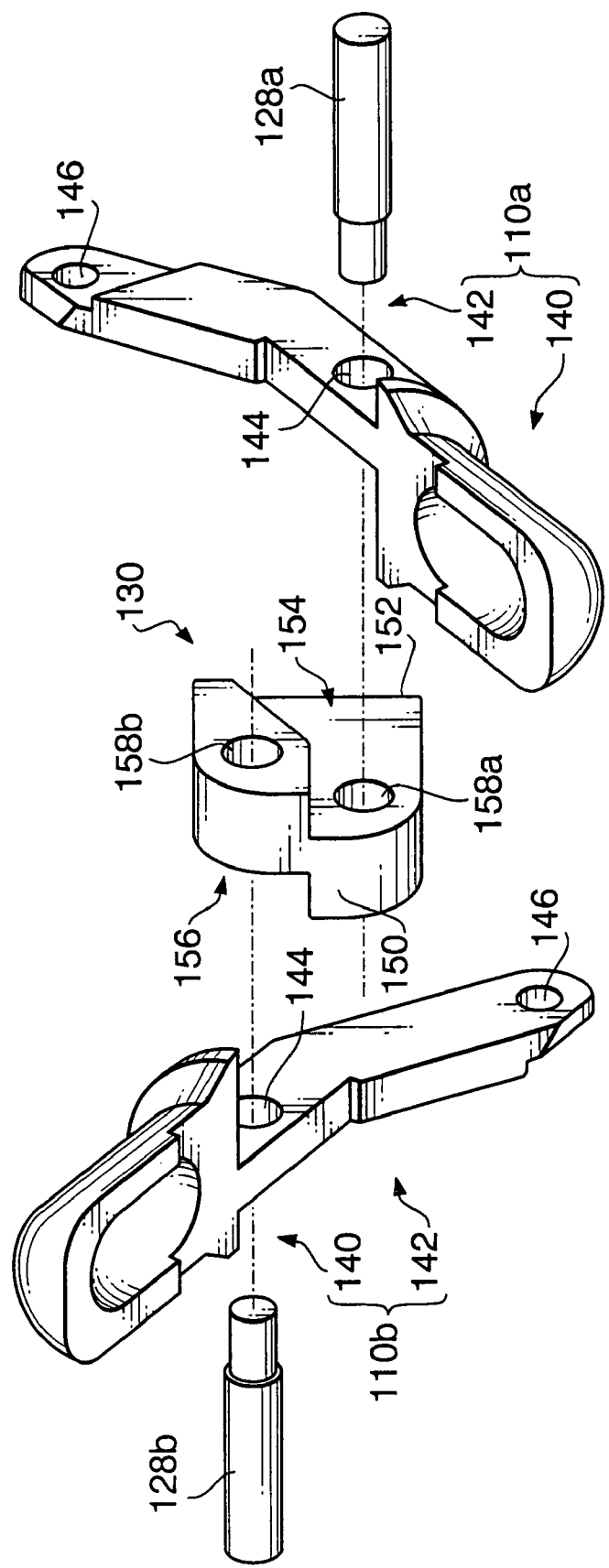
FIG. 5 is an exploded perspective view of a part of an electrode assembly of the bipolar hemostatic forceps shown in FIG. 1.

FIG. 5 is an exploded perspective view of the electrode assembly 109. Note that the supporting member 120 is not shown in FIG. 5 for clarity of the drawing.

Each of the first and second electrodes 110a and 110b is an elongated member made of conductive metal such as stainless steel. Each electrode (110a, 110b) includes an elongated front (distal) portion 140 and an elongated rear (proximal) portion 142. When the electrodes 110a and 110b are mounted to the supporting member 120, the front portions 140 thereof are located outside of the slit 124 and the rear portions 142 thereof are located between the two arms 122.

Two through holes are formed to the rear portion 142 of each electrode (110a, 110b). The first one is a supporting hole 144 provided at substantially the center of each electrode (110a, 110b). The other one is a connection hole 146 formed in the vicinity of the rear end of each electrode (110a, 110b).

The first electrode 110a is pivotably mounted to the supporting member 120 by inserting the first pin 128a through the supporting hole 144 thereof, while the second electrode 110b is pivotably mounted to the supporting member 120 by inserting the second pin 128b through the supporting hole 144 thereof.

The tip end of each conductive wire 108, which is exposed from the insulating tube 126, is passed through the connecting hole 146 and thereby connected with the corresponding electrode (110a, 110b).

The rear portion 142 of each electrode (110a, 110b) is slightly bent so that the conductive wires 108 sliding back and forth within the sheath 106 can swing the electrodes 110a and 110b around the respective pins 128a and 128b between the open and closed positions.

The front portion 140 of each electrode (110a, 110b) has a cup like shape. The electrodes 110a and 110b are arranged such that the cup like portions come in contact with each other at the concave sides thereof when the electrodes 110a and 110b are in the closed position.

The insulating block 130 is made of ceramic or resin such as poly-tetra-fluoro-ethylene. The insulating block 130 has front and rear sides (150, 152) and right and left sides (154, 156). The insulating block 130 is located within the slit 124 of the supporting member 120 such that the right and left sides (154, 156) face the right and left inner side surfaces 124a and 124b of the slit 124, respectively.

First and second through holes 158a and 158b are formed to the insulating block 130 which are perpendicular to the right and left sides 154 and 156 of the insulating block 130. The insulating block 130 is mounted to the supporting member 120 by inserting the first and second pins 128a and 128b through the first and second through holes 158a and 158b, respectively. Since the insulating block 130 is supported by two pins (128a, 128b), it does not rotate within the slit 124.

It should be noted that the through holes 158a and 158b have inner diameters slightly smaller than the outer diameter of the pins 128a and 128b. Accordingly, the pins 128a and 128b tightly fit into the respective through holes 158a and 158b and thereby prevent the electrode assembly 109 from disassembling.

FIGS. 6A and 6B show the right side 154 and the rear side 156 of the insulating block 130, respectively. Further, FIG. 7 is a sectional view of the electrode assembly 109 taken along the line VII—VII in FIG. 3A.

The right side 154 of the insulating block 130 is provided with a first protrusion 154a. The first protrusion 154a has a substantially flat side surface 154b. Similarly, the left side 156 of the insulating block 130 is provided with a second protrusion 156a. The second protrusion 156b has a substantially flat side surface 156b. The first and second protrusions 154a and 154b are formed such that the distance between the side surfaces 154b and 156b of the first and second protrusions 154a and 156a, or the total width of the insulating block 130, is substantially same as the width of the slit 124. Thus, the side surfaces 154b and 156b of the first and second protrusions 154a and 156a come in contact with the right and left inner side surface 124a and 124b of the slit 124 when the insulating block 130 is located in the slit 124.

As shown in FIG. 7, first and second protrusions 154a and 154b contribute to form first and second spaces 170a and 170b between the insulating block 130 and the arms 122 of the supporting member 120 for receiving the first and second electrodes 110a and 110b, respectively.

The first and second electrodes 110a and 110b are pivotably mounted to the first and second pins 128a and 128b within the first and second spaces 170a and 170b, respectively.

The first and second protrusions 154a and 156a are formed such that the widths of the first and second spaces 170a and 170b become slightly larger than the widths of the first and second electrodes 110a and 110b, respectively. Thus, the first and second electrode 110a and 110b can smoothly swing about the first and second pins 128a and 128b, respectively.

As can be seen in FIG. 7, the first protrusion 154a is formed such that it surrounds the second pin 128b in the vicinity of the first electrode 110a and the second protrusion 156a is formed such that it surrounds the first pin 128a in the vicinity of the second electrode 110b. The first and second protrusions configured as above prevent the first and second electrodes 110a and 110b from coming into contact with the second and first pins 128a and 128b, respectively, and making a short circuit.

Further, the first and second protrusions 154a and 154b are formed such that the first and second protrusions 154a and 154b abut against the rear portions 142 of the first and second electrodes 110a and 110b, respectively, when the electrodes 110a and 110b are swung toward the open position thereof as shown in FIG. 3B. In this way, the first and second protrusions 154a and 154b restrict the swinging angle of the electrodes 110a and 110b. Thus the front ends of the electrodes 110a and 110b do not open more than a predetermined distance which is within the range from 2 mm to 3 mm in the present embodiment. Thus, the hemostatic forceps 100 according to the present embodiment can pinch the bleeding portion within a body cavity without pinching also a large portion of the tissue around the bleeding portion. Accordingly, the hemostatic forceps 100 according to the present embodiment can carry out the hemostasis effectively.

FIG. 8 is a perspective view of a supporting member 200 which is a variation of the supporting member 120 and can be utilized in the hemostatic forceps 100 shown in FIGS. 1 through 7. FIG. 9 is a sectional view of the end portion of the hemostatic forceps 100 in which the supporting member 120 is replaced with the supporting member 200.

The supporting member 200 has a base portion 202 that is to be inserted into the flexible sheath 106 of the hemostatic forceps 100. The base portion 202 is formed in a cylindrical shape and is provided with a plurality of circumferential protrusions 202a. The circumferential protrusions 202a dig into the inner surface of the flexible sheath 106 as the base is inserted thereinto and thereby firmly connect the supporting member 200 with the flexible sheath 106. Two arms 204 are extending forwardly from the base to form a slit with a substantially constant width therebetween. Each of the arms 204 are provided with two bores 206 (only one for each arm is shown) at the front end portion through which the pins 128a and 128 can be inserted. An insulating block 208 that has essentially the same form as the insulating block 130 shown in FIG. 5 is integrally formed to the supporting member 200 between the front end portions of the two arms 204.

As described above, the supporting member 200 shown in FIG. 8 has essentially the same configuration as the supporting member 120 of the treatment tool shown in FIGS. 1 through 7 and differs therefrom only in that the insulating block 208 is integrally formed to the arms 204. The supporting member 200 configured as above has higher mechanical strength than the supporting member 120 since the insulating block 208 is integrally formed thereto, and enhance the strength of the electrode assembly 109 against external force. Further, since the supporting member 200 and the insulating block 208 are formed in one component, the electrode assembly 109 can be easily assembled.

In the hemostatic forceps 100 configured as above, the first and second electrodes 110a and 110b does not come into contact with each other except when the first and second electrodes 110a and 110b are moved to the closed position since the insulating block 130 is located between the first and second electrode 110a, 110b.

Further, the insulating block 130 supports the first and second pins 128a and 128b passed through the through holes 158a and 158b to prevent the first and second pins 128a from being bent and/or broken by the force exerted thereon from the first and second electrodes 110a and 110b as the first and second electrodes 110a and 110b are moved between the open and closed positions.

Further, since the insulating block 130 has substantially the same width as the slit 124, the arms 122 having the insulating block 130 therebetween do not bend inwardly even if external force is exerted on the arms 122, and hence the arms 122 do not make the first and second electrodes 110a and 110b immovable between the open and closed positions by strongly pressing them.

The insertion portion 104 of hemostatic forceps 100 configured as above is introduced into a body cavity such as a stomach through an endoscope and the first and second electrodes 110a and 110b are located in the vicinity of a bleeding portion.

Then, the operation portion 102 of the hemostatic forceps 100 is operated such that the pair of conductive wires 108 is slid forwards within the sheath 106 and swing the first and second electrodes 110a and 110b to the open position. Then, the electrodes 110a and 110b are moved by the endoscope such that bleeding portion is located between the electrodes 110a and 110b.

Next, the pair of conductive wires 108 are retracted by pulling back the rod portion 114 with respect to the cylindrical portion 112 to move the front portions 140 of the electrodes 110a and 110b to the closed position and thereby grasping the bleeding portion.

Next, a high frequency electrical power is supplied from the power supply 200 to the first and second electrodes 110a and 110b via the conductive wires 108. As a result, a high frequency current flows through the bleeding portion placed between the electrodes 110 to coagulate the bleeding portion and thereby stop bleeding therefrom.

The present disclosure relates to the subject matter contained in Japanese Patent Application No. P2002-106010, filed on Apr. 9, 2002, which is expressly incorporated herein by reference in its entirety.

What is claimed is:

1. A bipolar hemostatic forceps for an endoscope, comprising:
   an inserting portion configured to be inserted into a body cavity through the endoscope;
   first and second electrodes mounted to a distal end of said inserting portion, said first and second electrodes being movable between an open position and a closed position so as to be able to pinch a bleeding portion between front portions of said first and second electrodes, said open position and closed position defining swinging angles of said first and second electrodes, said first and second electrodes being supplied with high frequency electric power to generate high frequency current flowing through the bleeding portion pinched therebetween;
   an insulator located between said first and second electrodes to insulate said first and second electrodes from each other except at said front portions, said insulator having a shape that restricts the swinging angles of said first and second electrodes, wherein said insulator includes first and second side surfaces, said first and second side surfaces facing said first and second electrodes, respectively, said first and second side surfaces being provided with first and second protrusions, respectively, said first and second protrusions respectively abutting against said first and second electrodes to restrict the swinging angles of said first and second electrodes; and
   first and second pins penetrating said insulator through said first and second side surfaces, said first pin pivotably supporting said first electrode in the vicinity of said first side surface, said second pin pivotably supporting said second electrode in the vicinity of said second side surface;
   wherein said first protrusion of said insulator surrounds said second pin in the vicinity of said first electrode to prevent said first electrode from coming into contact with said second pin, and
   wherein said second protrusion of said insulator surrounds said first pin in the vicinity of said second electrode to prevent said second electrode from coming into contact with said first pin.

2. The bipolar hemostatic forceps according to claim 1, wherein said insulator is provided with two through holes having slightly smaller inner diameters than the outer diameters of said first and second pins, and said first and second pins penetrate said insulator by being inserted through said two through holes.

3. The bipolar hemostatic forceps according to claim 1, further comprising,
   a supporting member attached to a distal end of said inserting portion, said supporting member having two arms extending parallel to each other to form a slit therebetween, and
   wherein said insulator is integral with said supporting member within said slit with said first and second protrusions connected to said arms.

4. An electrode assembly to be mounted to a distal end of an inserting portion of a bipolar hemostatic forceps, said inserting portion configured to be inserted into a body cavity through an endoscope, comprising:
   a supporting member that is configured to be mounted to the distal end of the insertion portion of the bipolar hemostatic forceps;
   first and second electrodes held by said supporting member, said first and second electrodes being swingable to open and close front portions of said first and second electrodes, said open and close front portions defining swinging angles, said first and second electrodes being configured to be supplied with high frequency electric power to generate high frequency current between said front portions;
   an insulator located between said first and second electrodes to insulate said first and second electrodes from each other except at said front portions, said insulator having a shape that restricts the swinging angles of said first and second electrodes, wherein said insulator includes first and second side surfaces, said first and second side surfaces facing said first and second electrodes, respectively, said first and second side surfaces being provided with first and second protrusions, respectively, said first and second protrusions respectively abutting against said first and second electrodes to restrict the swinging angles of said first and second electrodes; and first and second pins penetrating said insulator through said first and second side surfaces, said first pin pivotably supporting said first electrode in the vicinity of said first side surface, said second pin pivotably supporting said second electrode in the vicinity of said second side surface;

wherein said first protrusion of said insulator surrounds said second pin in the vicinity of said first electrode to prevent said first electrode from coming into contact with said second pin, and wherein said second protrusion of said insulator surrounds said first pin in the vicinity of said second electrode to prevent said second electrode from coming into contact with said first pin.

5. The electrode assembly according to claim 4, wherein said insulator is provided with two through holes having slightly smaller inner diameters than the outer diameters of said first and second pins, and said first and second pins penetrate said insulator by being inserted through said two through holes.

6. The electrode assembly according to claim 4, wherein said supporting member has two arms extending parallel to each other to form a slit therebetween, and wherein said insulator is integral with said supporting member within said slit with said first and second protrusions connected to said arms.

7. A bipolar hemostatic forceps for an endoscope, comprising:

an inserting portion configured to be inserted into a body cavity through the endoscope;

first and second electrodes mounted to a distal end of said inserting portion, said first and second electrodes being movable between an open position and a closed position so as to be able to pinch a bleeding portion between front portions of said first and second electrodes, said first and second electrodes being supplied with high frequency electric power to generate high frequency current flowing through the bleeding portion pinched therebetween; and an insulator located between said first and second electrodes to insulate said first and second electrodes from each other except at said front portions, said insulator comprising a first protrusion which restricts a swinging angle of said first electrode, and a second protrusion which restricts a swinging angle of said second electrode, wherein a pivoting axis of said first electrode passes through said second protrusion, and a pivoting axis of said second electrode passes through said first protrusion.

8. The bipolar hemostatic forceps according to claim 7, further comprising:

first and second pins penetrating said insulator through said first and second protrusions, said first pin pivotably supporting said second electrode through said first protrusion, and said second pin pivotably supporting said first electrode through said second protrusion.

9. The bipolar hemostatic forceps according to claim 7, further comprising:

a supporting member attached to a distal end of said inserting portion, said supporting member having two arms extending in parallel to each other to form a slit therebetween, said first and second protrusions connecting to said arms.

* * * * *